(12) United States Patent
Takaiwa et al.

(10) Patent No.: US 7,595,384 B2
(45) Date of Patent: Sep. 29, 2009

(54) SEED-SPECIFIC GENE PROMOTER FROM THE RICE 10 KDA PROLAMININ GENE AND USES THEREOF

(75) Inventors: Fumio Takaiwa, Tsukuba (JP); Leqing Qu, Tsukuba (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 11/644,759

(22) Filed: Dec. 22, 2006

(65) Prior Publication Data

US 2007/0118933 A1 May 24, 2007

Related U.S. Application Data

(62) Division of application No. 11/414,882, filed on May 1, 2006, which is a division of application No. 10/978,798, filed on Nov. 1, 2004, now Pat. No. 7,192,774.

(30) Foreign Application Priority Data

Oct. 31, 2003 (JP) .............................. 2003-373815

(51) Int. Cl.
  C07H 21/04 (2006.01)
  C12N 15/82 (2006.01)
  C12N 5/04 (2006.01)
  A01H 5/00 (2006.01)
(52) U.S. Cl. .................. 536/24.1; 435/320.1; 435/419; 435/468; 800/287; 800/298; 800/278
(58) Field of Classification Search ........................ None
See application file for complete search history.

(56) References Cited

U.S. PATENT DOCUMENTS

| 5,294,593 | A | * | 3/1994 | Khan .......................... 504/100 |
|---|---|---|---|---|
| 7,332,318 | B2 | | 2/2008 | Shimizu et al. |
| 7,402,418 | B2 | | 7/2008 | Osumi et al. |
| 2002/0081590 | A1 | | 6/2002 | Penn et al. |
| 2003/0135884 | A1 | | 7/2003 | Yu et al. |
| 2003/0159182 | A1 | | 8/2003 | Tackaberry et al. |
| 2005/0066387 | A1 | | 3/2005 | Yu et al. |
| 2005/0223438 | A1 | | 10/2005 | Otsuki et al. |
| 2006/0191044 | A1 | * | 8/2006 | Takaiwa et al. .............. 800/287 |
| 2007/0136896 | A1 | | 6/2007 | Takaiwa et al. |

FOREIGN PATENT DOCUMENTS

| EP | 1 577 384 | | 9/2005 |
|---|---|---|---|
| JP | 2002-58492 | | 2/2002 |
| JP | 2002-209462 | | 7/2002 |
| JP | 2002-315582 | | 10/2002 |
| JP | 2003-33190 | | 4/2003 |
| JP | 2004-159638 | | 6/2004 |
| WO | WO 99/16890 | * | 4/1999 |
| WO | WO 03/000905 | | 1/2003 |
| WO | WO 03/079769 | | 10/2003 |
| WO | WO 2004/094637 | | 4/2004 |
| WO | WO 2004/056993 | | 7/2004 |

OTHER PUBLICATIONS

Donald et al. Mutation of either G box or I box sequences profoundly affects expression from the Arabidopsis rbcS-1A promoter. (1990) The EMBO Journal, vol. 9, pp. 1717-1726.*
Benfey et al. The Cauliflower Mosaic Virus 35S promoter: combinatorial regulation of transcription in plants. (1990) Science, vol. 250, pp. 959-966.*
Kim et al. A 20 nucleotide upstream element is essential for the nopaline synthase (nos) promoter activity. (1994) PMB, vol. 24, pp. 105-117.*
Feng et al. Nucleotide sequence of a cloned rice genomic DNA fragment that encodes a 10 kDa prolamin polypeptide. (1990) Nucleic Acids Research, vol. 18, p. 683.*
Feng et al. (1993) GenBank Accession X17074, pp. 1-2.*
Lazo et al. A DNA transformation-competent arabidopsis genomic library in agrobacterium. (1991) Biotechnology; vol. 9, pp. 963-967.*
Donald, et al. "Mutation of Either G Box or I Box Sequences Profoundly Affects Expression from the Arabidopsis rbcS-1A Promoter," *The Embo Journal*, vol. 9, pp. 1717-1726, 1990.
Benfey, et al. The Cauliflower Mosaic Virus 35S Promoter: Combinatorial Regulation of Transcription in Plants, *Science*, vol. 250, pp. 959-966, 1990.
Jiang, et al. "New Rice Gluetelin Gene GluB-4," GenBank Accession AF537221, pp. 1-3, 2002.
Sasaki, et al. *Oryza Sativa Nipponbare* (GA3) Genomic DNA, Chromosome 2, BAC Clone: OJ1005_D05, GenBank Accession AP004128, pp. 1-26, 2002.
Katsube, et al. "Accumulation of Soybean Glycinin and Its Assembly with the Glutelins in Rice," *Plant Physiology*, vol. 120, pp. 1063-1073, Aug. 1999.
Takaiwa, et al. "Sequence of Three Members and Expression of a New Major Subfamily of Glutelin Genes from Rice," *Plant Molecular Biology*, vol. 17, pp. 875-885, 1991.
Takaiwa, et al. "Genomic DNA Sequences of Two New Genes for New Storage Protein Glutelin in Rice," *Japanese Journal of Genetics*, vol. 66, pp. 161-171, 1991.
Washida, et al. "Identification of *cis*-Regulatory Elements Required for Endosperm Expression of the Rice Storage Protein Glutelin Gene GluB-1," *Plant Molecular Biology*, vol. 40, pp. 1-12, 1999.

(Continued)

Primary Examiner—Cathy Kingdon Worley
(74) Attorney, Agent, or Firm—Knobbe, Martens, Olson & Bear, LLP

(57) ABSTRACT

An objective of the present invention is to provide a promoter from the rice 10 kDa Prolaminin gene having seed-specific promoter activity, and methods of expressing foreign proteins in seeds. The present inventors isolated the promoters of a number of genes that are expressed in rice seeds, constructed binary vectors in which each promoter is inserted upstream of the GUS reporter gene, and transformed rice using the *Agrobacterium* method. The inventors then used GUS expression level as an index to examine the site of expression, the expression pattern during seed maturation, and the level of expression in seeds for each promoter. They thus discovered promoters with activity specific to a particular site in seeds, and with higher activity than constitutive promoters and known seed-specific promoters.

23 Claims, 6 Drawing Sheets

OTHER PUBLICATIONS

Croissant-Sych, et al. "Identification of Positive and Negative Regulatory cis-Elements of the Rice Glutelin Gt3 Promoter," Plant Science, vol. 116, pp. 27-35, 1996.

Daniell, et al. "Medical Molecular Farming: Production of Antibodies, Biopharmaceuticals and Edible Vaccines in Plants," Trends in Plant Science, vol. 6, No. 5, pp. 219-226, May 2001.

Delaney, "Choice of Crop Species and Development of Transgenic Product Lines," in Plants as Factories for Protein Production, pp. 139-158 E. Hood and J. Howard, editors, Kluwer Academic Publishers, 2002.

Fischer, et al. "Molecular Farming of Pharmaceutical Proteins," Transgenic Research, vol. 9, pp. 279-299, 2000.

Giddings et al. "Transgenic Plants as Factories for Biopharmaceuticals," Nature Biotechnology, vol. 18, pp. 1151-1155, Nov. 2000.

Howard, et al., "Introduction to Molecular Farming," Plants as Factories for Protein Production, pp. vii-x, E. Hood and J. Howard, editors, Kluwer Academic Publishers, 2002.

Takaiwa, et al. "Characterization of Common cis-Regulatory Elements Responsible for the Endosperm-Specific Expression of Members of the Rice Glutelin Multigene Family," Plant Molecular Biology, vol. 30, pp. 1207-1221, 1996.

Takaiwa, et al. "Analysis of the 5" Flanking Region Responsible for the Endosperm-Specific Expression of a Rice Glutelin Chimeric Gene in Transgenic Tobacco," Plant Molecular Biology, vol. 16, pp. 49-58, 1991.

Walmsley, et al. "Plants for Delivery of Edible Vaccines," Plant Biotechnology, vol. 11, No. 2, pp. 126-129, 2000.

Wu, et al. "Quantitative Nature of the Prolamin-box, ACGT and AACA Motifs in a Rice Glutelin Gene Promoter: Minimal cis-Element Requirements for Endosperm-Specific Gene Expression," The Plant Journal, vol. 23, No. 3, pp. 415-421, 2000.

Wu, et al. "The GCN4 Motif in a Rice Glutelin Gene is Essential for Endosperm-Specific Gene Expression and is Activated by Opaque-2 in Transgenic Rice Plants," The Plant Journal, vol. 14, No. 6, pp. 673-683, 1998.

Yoshihara et al. "A 45-bp proximal Region Containing AACA and GCN4 Motif is Sufficient to Confer Endosperm-Specific Expression of the Rice Storage Protein Glutelin Gene, GluA-3," FEBS Letters, vol. 383, pp. 213-218, 1996.

Zhao et al. "Tissue-Specific Expression and Temporal Regulation of the Rice Glutelin Gt3 Gene Are Conferred by at Least Two Spatially Separated cis-Regulatory Elements," Plant Molecular Biology, vol. 25, pp. 429-436, 1994.

Zheng, et al. "5' Distal and Proximal cis-Acting Regulator Elements are Required for Developmental Control of a Rice Seed Storage Protein Glutelin Gene," The Plant Journal, vol. 4, No. 2, pp. 357-366, 1993.

Kikuchi, et al. Molecular Characterization of a Gene for Alanine Aminotransferase from Rice (Oryza sativa) Plant Molecular Biology, vol. 39, pp. 149-159, 1999.

Patel, et al. "Transgenic Barley Expressing a Fungal Xylanase Gene in the Endosperm of the Developing Grains," Molecular Breeding, vol. 6, pp. 113-123, 2000.

Qu, et al. "Evaluation of Tissue Specificity and Expression Strength of Rice Seed Component Gene Promoters in Transgenic Rice," Plant Biotechnology Journal, vol. 2, pp. 113-125, 2004.

Wu, et al. "Promoters of Rice Seed Storage Protein Genes Direct Endosperm-Specific Gene Expression in Transgenic Rice," Plant Cell Physiology, vol. 39, No. 8, pp. 885-889, 1998.

Kim, et al. A 20 Nucleotide Upstream Element is Essential for the Nopaline Synthase (nos) Promoter Activity. (1994) PMB, vol. 24, pp. 105-117.

Fumio. O. sativa BluB-1 Gene for Glutelin. (1991) GenBank Accession #X54314.

Su, et al. Oryza sativa 10 kDa Prolamin Gene, complete cds. (2001) GenBank Accession #AF294580.

Sun, et al. "Rice Embryo Globulins: Amino-terminal Amino Acid Sequences, cDNA Cloning and Expression," Plant Cell Physiology, vol. 37, No. 5, pp. 612-620, 1996.

Lazo, et al. "A DNA Transformation-Competent Arabidopsis Genomic Library in Agrobacterium," Biotechnology, vol. 9, pp. 963-967, Oct. 1991.

Stålberg, et al. "Deletion Analysis of a 2S Seed Storage protein Promoter of Brassica napus in Transgenic Tobacco," Plant Molecular Biology, vol. 23, pp. 671-683, 1993.

Chen, et al. "Oryza sativa subsp. japonic putative ADP-Glucose Phrophosphorylase Subunit SH2 . . . " GenBank Accession AF101045, pp. 1-12.

Russell, et al. "Tissue-Specific Expression in Transgenic Maize of Four Endosperm Promoters from Maize and rice," Transgenic Research, vol. 6, pp. 157-168, 1997.

* cited by examiner

SEED-SPECIFIC GENE PROMOTER FROM THE RICE 10 KDA PROLAMININ GENE AND USES THEREOF

RELATED APPLICATIONS

This application is a divisional of U.S. application Ser. No. 11/414,882, filed May 1, 2006 which is a divisional application of U.S. application Ser. No. 10/978,798, filed Nov. 1, 2004 now U.S. Pat. No. 7,192,774 which claims priority to JP 2003-373815, filed Oct. 31, 2003. All of the above applications are incorporated herein by reference in their entirety.

FIELD OF THE INVENTION

This invention relates to seed-specific gene promoters and uses thereof.

BACKGROUND OF THE INVENTION

Recombinant DNA technology is being implemented as a way of improving plant breeds. Using this technology, plants with additional functions such as herbicide resistance, pest insect resistance, and the like have been created, and progress is being made in their practical application. The use of recombinant technologies to improve plant breeds not only aims to add new functions to plants: there has been much research and development into the expression of useful proteins in plants, by introducing these plants with a foreign gene. Such research uses plants as factories to produce useful proteins.

Production of recombinant proteins in plants has many advantages, the most evident of which are the reduced cost compared to systems that utilize transgenic animals; the ease with which scale of production can be adjusted to suit market size; and the absence of any risk of contamination by animal-borne pathogens such as viruses and prions (Daniell et al., Trends Plant Sci., 6, 219-226 (2001); Fischer and Emans, Transgenic Research, 9, 279-299 (2000); Giddings et al., Nature Biotech., 18, 1151-1156 (2000)).

Recently, systems using seeds for production of recombinant protein in plants have been shown to be more advantageous than those using leaves or roots (Delaney, 2002, Plants as Factories for Protein Production (Hood, E. E. and Howard, J. A) pp. 139-158 (2002). Netherlands: Kluwer Academic; Howard and Hood, Plants as Factories for Protein Production (Hood, E. E. and Howard, J. A) pp. vii-x (2002). Netherlands: Kluwer Academic). Seeds are storage organs, in which a special organelle called a protein body stably stores a large amount of a small number of storage proteins. This feature has been employed by using seeds as ideal bioreactors for producing recombinant protein. Recombinant proteins accumulated in seeds are very stable, and can be administered orally without any need for further processing or purification. Antibodies or vaccines expressed in seeds are reported to be highly stable, and can be stored for years, even at room temperature, without decomposition. Moreover, vaccines administered via seeds are thought to trigger antibody production by the mucosal immune system, without processing or purification (Walmsley and Arntzen, Curr. Opin. Biotech., 11, 126-129 (2000)).

When producing proteins using recombinant technology, the yield of a protein of interest is affected by many factors, including transcription factors. The most important and easily controlled of these factors is the choice of promoter. In order to use rice seeds as a platform for recombinant protein production, it is important to use a promoter suited to the needs of individual proteins and their use in biotechnology. This is because the promoter controls the timing, location and level of expression.

However, analyses of the cis-regulatory factors involved in endosperm-specific expression are limited to those of a small number of glutelin genes, using different species (transgenic tobacco) and the same species (transgenic rice). (Croissant-Sych and Okita, Plant Sci., 116, 27-35 (1996); Takaiwa et al., Plant Mol. Biol., 16, 49-58 (1991a); Takaiwa et al., Plant Mol. Biol., 30, 1207-1221 (1996); Wu et al., Plant J., 14, 673-983 (1998a); Wu et al., Plant J., 23, 415-421 (2000); Yoshihara et al., FEBS Lett., 383, 213-218 (1996); Zhao et al., Plant Mol. Biol., 25, 429-436 (1994); Zheng et al., Plant J., 4, 357-366 (1993)). Studies of a few other rice storage protein promoters were no more than observations of their spatial expression patterns (Wu et al., Plant Cell Physiol., 39, 885-889 (1998b)).

SUMMARY OF THE INVENTION

The present invention has been made considering the above circumstances. An objective of the present invention is to provide promoters with seed-specific promoter activity, and methods of expressing foreign proteins in seeds. Another objective is to provide promoters with specific promoter activity in a particular site, such as the seed endosperm, embryo, and aleurone layer.

In order to achieve the above objectives, the present inventors isolated a number of promoters of rice genes expressed in seeds, and constructed binary vectors in which each promoter was inserted upstream of GUS reporter gene. The present inventors then transformed rice using the *Agrobacterium* method. Then, for each promoter, the inventors used GUS expression as an index to examine the site of expression, the expression pattern during seed maturation, and the level of expression in seeds. They thus discovered promoters with an activity of expression specific to a particular site in seeds, and with higher activity than constitutive promoters and known seed-specific promoters. As described above, it is useful for a seed expressing a foreign gene product to be taken as food. However, for this to be possible, the foreign gene must be expressed in an edible part of the seed. For example, in one of the main cereals, rice, the endosperm is normally eaten, and therefore the above goal would be achieved by using an endosperm-specific promoter in rice. Furthermore, promoters specific for a particular site in a seed will enable expression of a foreign gene at a desired place in a seed. Therefore, these promoters can be valuable tools for metabolic engineering using seeds. For example, using a promoter that directs expression in the aleurone layer or embryo may control fatty acid metabolism.

Thus, the present invention relates to promoters specific to a particular site in a seed, and to uses thereof. More specifically, it provides:

(1) a DNA comprising promoter activity in seeds, wherein the DNA is any one of the following (a) to (c):
  (a) a DNA comprising a nucleotide sequence of any one of SEQ ID NOs: 1 to 7,
  (b) a DNA comprising a nucleotide sequence wherein one or more nucleotides are added, deleted, substituted, or inserted into a nucleotide sequence of any one of SEQ ID NOs: 1 to 7, and
  (c) a DNA that hybridizes under stringent conditions with a DNA comprising a nucleotide sequence of any one of SEQ ID NOs: 1 to 7;

(2) a DNA comprising a gene functionally linked downstream of the DNA of (1);

(3) a vector comprising the DNA of (1) or (2);

(4) a transformed plant cell carrying the DNA of (2);
(5) a transformed plant cell introduced with the vector of (3);
(6) a transformed plant carrying the cell of (4) or (5);
(7) a reproductive material of the plant of (6);
(8) the reproductive material of (7), wherein the reproductive material is a seed; and
(9) a method of expressing a gene in a seed generated from a plant cell, comprising the steps of:
  (a) introducing the DNA of (2) or the vector of (3) into the plant cell, and
  (b) regenerating a plant from the plant cell.

In certain preferred embodiments, the isolated DNA described above further includes a 3'-untranslated region as shown in SEQ ID NO: 8.

Certain embodiments of the invention are directed to an isolated DNA which confers seed-specific gene expression, where the DNA is any one of the following (a) to (c):
  (a) a DNA which includes a nucleotide sequence of SEQ ID NO: 8,
  (b) a DNA which includes a nucleotide sequence where one or more nucleotides are added, deleted, substituted, or inserted into a nucleotide sequence of SEQ ID NO: 8, and
  (c) a DNA that hybridizes under stringent conditions with a DNA which includes a nucleotide sequence of SEQ ID NO: 8. Also included in certain embodiments of the invention is a vector which includes an isolated DNA as described above.

A preferred embodiment of the invention is directed to a vector which includes the promoter of SEQ ID NO: 3 and the 3'-untranslated region of SEQ ID NO: 8.

DETAILED DESCRIPTION OF THE INVENTION

Figure 1:
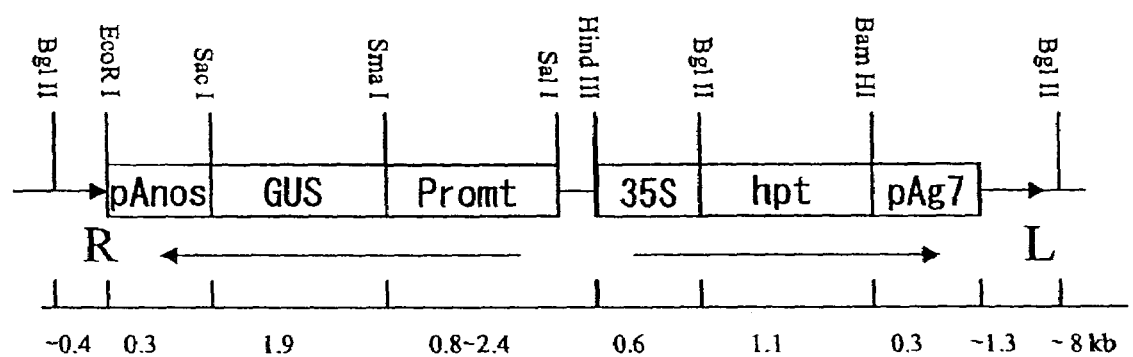
FIG. 1 shows a diagram of the construction of the chimeric gene used for rice transformation. The 5'-flanking regions of various genes encoding rice seed storage proteins and non-storage proteins were fused into a region between two restriction sites, selected from HindIII, SalI, and SmaI sites. The GUS reporter gene and the Nos terminator were then fused. The promoter was shown to promote the genes: 1.3 kb GluB-1, 2.3 kb GluB-1, GluB-2, GluB-4, 10 kDa prolamin, 13 kDa prolamin (PG5), 16 kDa prolamin, 26 kDa Glb-1, REG2, Ole18, soybean β-conglycinin, AlaAT, GOGAT, PPDK, AGPase, and SBE1.

The present invention provides novel DNAs with promoter activity in seeds. This invention, as described above, is based on the discovery by the present inventors of promoters with promoter activity specific to particular sites in seeds, and that exhibit greater activity than constitutive promoters and known seed-specific promoters.

Specifically, the above DNAs of the present invention include DNAs with promoter activity that comprise a sequence of any of SEQ ID NOs: 1 to 7. The present inventors identified these DNAs as novel rice-derived DNAs comprising promoter activity, and grouped them into the following three groups:

Promoter DNAs specific to the endosperm (the nucleotide sequences of the respective DNAs are shown in SEQ ID NOs: 1 to 4).

Promoter DNAs specific to embryo or aleurone tissue (the nucleotide sequences of the respective DNAs are shown in SEQ ID NOs: 5 and 6).

Promoter DNAs for expression in the entire seed (the nucleotide sequence of the DNA is shown in SEQ ID NO: 7).

Group (A), the endosperm-specific promoter DNA group, comprises the rice glutelin GluB-1 gene promoter (SEQ ID NO: 1), rice glutelin GluB-4 gene promoter (SEQ ID NO: 2), 10 kDa prolamin promoter (SEQ ID NO: 3), and 16 kDa prolamin promoter (SEQ ID NO: 4). Expression of this group can be observed in aleurone and sub-aleurone tissues at seven days after flowering, and progressively spreads into the inner endosperm region during maturation. This expression pattern does not change during the maturation process.

Group (B), the embryo or aleurone tissue-specific promoter DNA group, comprises the rice embryo globulin gene promoter (SEQ ID NO: 5), and rice oleosin promoter (SEQ ID NO: 6). This group shows expression in the aleurone tissue in the early stages of maturation (seven days after flowering), and the expression spreads into the embryo and aleurone tissue during maturation, but not to the endosperm.

Group (C), promoter DNAs for expression in the entire seed, comprises the rice ADP-glucose pyrophosphorylase gene promoter (SEQ ID NO: 7). This promoter first shows expression in the embryo in the early stage of maturation, and then in the entire seed during maturation (expression in the embryo is also extremely high in the late stage of maturation).

One skilled in the art can use conventional methods to prepare DNAs comprising the seed-specific promoters of groups (A) to (C) (hereinafter abbreviated as "the DNAs of this invention"). For example, the DNAs can be prepared by designing an appropriate pair of primers based on a nucleotide sequence of any of SEQ ID NOs: 1 to 7 (for example, SEQ ID NOs: 9 to 22), and performing PCR using a rice genomic DNA as the template, and screening a genomic library with the resulting amplified DNA fragment as a probe. Moreover, a commercially available DNA synthesizer may be used to synthesize a desired DNA.

The DNAs of this invention may be used to obtain (isolate) DNAs comprising promoter activity. In the first step of isolating a DNA, a DNA of this invention or its part may be used as a probe, or an oligonucleotide that specifically hybridizes with a DNA of the invention may be used as a primer to isolate a DNA comprising high homology with the above DNA from a desired organism. The DNAs of this invention also comprise DNAs that hybridize with DNAs comprising a nucleotide sequence of any of SEQ ID NOs: 1 to 7, which can be isolated using standard hybridization techniques (Southern E.M., J. Mol. Biol., 98, 503 (1975)) or PCR methods (Saiki R. K. et al., Science, 230, 1350 (1985); Saiki R. K. et al., Science, 239, 487 (1988)). Thus, it is feasible for one skilled in the art to isolate from a desired organism a DNA high homologous to a DNA comprising a nucleotide sequence of any of SEQ ID NOs: 1 to 7, using a DNA comprising a nucleotide sequence of any of SEQ ID NOs: 1 to 7 or its part as a probe, or an oligonucleotide that specifically hybridizes with a DNA comprising a nucleotide sequence of any of SEQ ID NOs: 1 to 7 as a primer. In order to isolate such DNAs, hybridization is preferably performed under stringent conditions. Hybridization may be performed with buffers that permit the formation of a hybridization complex between nucleic acid sequences that contain some mismatches. At high stringency, hybridization complexes will remain stable only where the nucleic acid molecules are almost completely complementary. Many factors determine the stringency of hybridization, including G+C content of the cDNA, salt concentration, and temperature. For example, stringency may be increased by reducing the concentration of salt or by raising the hybridization temperature. Temperature conditions for hybridization and washing greatly influence stringency and can be adjusted using melting temperature (Tm). Tm varies with the ratio of constitutive nucleotides in the hybridizing base pairs, and with the composition of the hybridization solution (concentrations of salts, formamide and sodium dodecyl sulfate). In solutions used for some membrane based hybridizations, addition of an organic solvent, such as formamide, allows the reaction to occur at a lower temperature. Accordingly, on considering the relevant parameters, one skilled in the art can select appropriate conditions to achieve a suitable stringency based experience or experimentation. Herein, stringent hybridization conditions mean conditions using 6 M urea, 0.4% SDS, and 0.5×SSC, or those using 0.1% SDS (60° C., 0.3 M NaCl, 0.03 M sodium citrate), or conditions providing an equivalent stringency. Under more stringent conditions, for example, performing hybridization in 6 M urea, 0.4% SDS, and 0.1× SSC, one can expect to isolate DNAs with higher homology. High homology means sequence identity over the entire nucleotide sequence of preferably 50% or higher, more preferably, the isolated DNA is at least about 65%, 70%, 75%, 80%, 85%, 90%, 91%, 92%, 93%, 94%, 95%, 96%, 97%, 98%, 99%, or more, identical.

To determine the percent identity of two DNAs, the sequences are aligned for optimal comparison purposes. The percent identity between the two sequences is a function of the number of identical positions shared by the sequences. The percent identity between two sequences can be determined using conventional techniques such as to those described herein, with or without allowing gaps. In calculating percent identity, typically exact matches are counted. For example, when an isolated DNA of the present invention is longer than or equivalent in length to a prior art sequence, the comparison is made with the full length of the inventive sequence. Alternatively, when an isolated DNA of the present invention is shorter than the prior art sequence, the comparison is made to a segment of the prior art sequence of the same length as that of the inventive sequence (excluding any loop required by the homology calculation).

Identity between nucleotide sequences can be determined by using the BLAST algorithm developed by Karlin and Altschul (Proc. Nati. Acad. Sci. U.S.A., 87, 2264-2268 (1990); Karlin S. and Altschul S. F., Proc. Natl. Acad. Sci. U.S.A., 90, 5873). A program called BLASTN has been developed based on the BLAST algorithm (Altschul S. F. et al., J. Mol. Biol., 215, 403 (1990)). When analyzing nucleotide sequence using BLASTN, parameters may be set as score=100 and wordlength=12, for example. When using the BLAST and Gapped BLAST programs, the default parameters for each program may be chosen. Specific procedures for these analyses are publicly known. Another example of a mathematical algorithm that may be utilized for the comparison of sequences is the algorithm of Myers and Miller (1988) CABIOS 4:11-17.

The DNAs of this invention are normally derived from plants, preferably from monocotyledons, and more preferably from Poaceae, but are not limited to any particular origin, as long as the DNA has seed-specific promoter activity.

In addition, this invention provides DNAs that are structurally similar to the above DNAs, and comprise promoter activity. Such DNAs include DNAs with seed specific promoter activity that comprise a nucleotide sequence wherein one or more nucleotides are substituted, deleted, added, and/or inserted into a nucleotide sequence of any of SEQ ID NOs: 1 to 7. Such DNAs can also be used to isolate a DNA of this invention that comprises promoter activity. Methods for preparing such DNAs are well known to those skilled in the art, and include the hybridization techniques and polymerase chain reaction (PCR), as described above. Furthermore, the above DNAs may be prepared by introducing mutations into DNAs comprising a nucleotide sequence of any of SEQ ID NOs: 1 to 7, for example, by using site-directed mutagenesis method (Kramer W. and Fritz H. J., Methods Enzymol., 154, 350 (1987)).

One skilled in the art can determine whether or not the DNAs prepared as above comprise promoter activity by using methods such as known reporter assays using reporter genes. Reporter genes are not limited to any particular gene, as long as their expression is detectable. For example, reporter genes may be those routinely used by those skilled in the art, such as CAT gene, lacZ gene, luciferase gene, β-glucuronidase (GUS) gene, and GFP gene.

The reporter gene expression level can be measured by the methods commonly known to those skilled in the art, depending on the type of reporter gene. For example, when CAT gene is used as the reporter gene, the expression level of the reporter gene can be measured by detecting acetylation of chloramphenicol by the gene product. When lacZ gene is used as the reporter, expression level can be measured by detecting the color of a dye compound produced by the catalytic function of the gene product. In the case of luciferase gene, expression level can be measured by detecting fluorescence from a fluorescent compound produced by the catalytic function of the gene product; the GUS reporter gene expression can be measured by detecting luminescence of Glucuron (ICN), or the color of 5-bromo-4-chloro-3-indolyl-β-glucuronide (X-Gluc) as the result of catalytic function of the gene product. Furthermore, GFP expression can be measured by detecting the fluorescence of GFP protein.

In addition, if a gene other than those described above is used as a reporter, the expression level of the gene can be measured by methods known to those skilled in the art. For example, mRNAs may be extracted by standard methods, and then used as templates to perform Northern hybridization or RT-PCR to measure the transcription level of the gene. Furthermore, DNA array technology may be used to measure gene transcription levels. In addition, fractions containing proteins encoded by the genes may be recovered by standard methods, and expression of the protein of the present invention may be detected by electrophoresis, such as SDS-PAGE, to measure the translation level of the gene. Furthermore, the expression of the protein encoded by a gene may be detected by Western blotting, using an antibody against the protein to measure its translation level. The antibody used to detect the protein encoded by the gene can be any antibody, and is not particularly limited as long as it is detectable. For example, both monoclonal antibodies or polyclonal antibodies may be used. The antibody can be prepared by methods known to those skilled in the art.

Furthermore, the present invention provides DNAs in which an arbitrary gene is functionally linked downstream of an above promoter DNA. The DNAs of the invention enable specific expression of a desired protein or peptide, encoded by an arbitrary gene, in seeds, by activating a promoter DNA.

Herein, "functionally linked" means that a DNA of the invention and a gene are linked to each other such that expression of the downstream gene is triggered by binding of a transcription factor to a DNA with promoter activity of the present invention. Thus, even if the gene is linked with another gene, and forms a fusion protein with the product of the other gene, it is collectively considered to be "functionally linked" as long as expression of the fusion protein is induced when a transcription factor binds to the DNA of this invention.

The present invention also provides vectors comprising a DNA (referred to below as "the above DNA"), wherein an arbitrary gene is functionally linked to an above promoter DNA or downstream of it. The vectors of this invention are useful for maintaining the above DNA in host cells, or for expressing a protein of interest and such by transforming plants.

The vectors used for insertion of the above DNA are not limited to any particular vector as long as they enable expression of the inserted gene in plant cells. For example, vectors comprising a promoter for constitutive gene expression in plant cells (for example, cauliflower mosaic virus 35S promoter), or vectors comprising a promoter that can be activated by an external stimuli in an inducible manner, can be used. Vectors comprising the above DNA as an insert may be introduced into plant cells by methods commonly known to those skilled in the art, such as polyethylene glycol methods, electroporation methods, *Agrobacterium*-mediated methods, and particle gun methods. *Agrobacterium*-mediated methods may be performed, for example, by the method of Nagel et al. (Microbiol. Lett., 67, 325 (1990)), by introducing an expression vector comprising the above DNA as an insert into *Agrobacterium*, and infecting plant cells with the *Agrobacterium* by direct infection or the leaf disc method, to introduce the above DNA into plant cells.

In addition, the present invention provides transformed plant cells into which the above DNA or vector is introduced. The transformed plant cells of the present invention can be any form of plant cell, or a cluster of plant cells into which the above DNA or vector is introduced, as long as the cells can regenerate a plant. For example, the plant cells of the present invention comprise suspensions of cultured cells, protoplasts, leaf sections, and calluses.

Vectors can be introduced into plant cells by a variety of methods commonly known to those skilled in the art, such as by polyethylene glycol methods, electroporation methods, *Agrobacterium*-mediated methods, and particle gun methods.

Furthermore, the present invention provides transformed plants carrying the above-described cells. The plants of the invention can be used in systems for producing a desired gene product.

Plants can be regenerated from transformed plant cells using methods known commonly to those skilled in the art, according to the type of plant. For example, rice may be regenerated by the method of Fujimura et al. (Plant Tissue Culture Lett., 2, 74 (1995)), corn may be regenerated by the method of Shillito et al. (Bio/Technology, 7, 581 (1989)) or the method of Gorden-Kamm et al. (Plant Cell, 2, 603 (1990)), and potato may be regenerated by the method of Visser et al. (Theor. Appl. Genet., 78, 594 (1989)). *Arabidopsis* may be regenerated by the method of Akama et al. (Plant Cell Reports, 12, 7-11 (1992)), and eucalyptus may be regenerated by the method of Doi et al. (JP-A Hei 8-89113).

Furthermore, the present invention provides not only plants carrying cells into which the above DNA has been introduced, but also the reproductive materials of those plants. After obtaining transformed plants that have the above DNA or vector introduced in their genome, reproductive materials (for example, seeds, fruits, cuttings, tubers, tuberous roots, shoots, calluses, and protoplasts) can be obtained, and the plants can be mass-produced from these sources. In particular, in addition to being a reproductive material, seeds are places where the above introduced promoter causes accumulation of foreign gene product.

Furthermore, the present invention provides methods of expressing an arbitrary gene in plant seed cells. The methods of the invention comprise the steps of introducing plant cells with a DNA in which an arbitrary gene is functionally linked downstream of the above promoter DNA of the invention, or the above vector of this invention, and regenerating a plant from the plant cells. The steps of introduction into plant cells and regeneration of a plant can be performed by the above methods. The methods of the invention may be used to obtain a desired gene product from a plant, or to obtain seeds that accumulate the desired gene product. Plants regenerated using a desired gene by a method of this invention bear seeds that accumulate the product of the desired gene. Thus, the gene product can be obtained by purification from these seeds, or such. In addition, if the desired gene product is a medicinal compound or the like, seeds can be used as a final form, omitting purification steps, because seeds can be ingested as is.

As used herein, an "isolated promoter" is a promoter removed from its original environment (e.g., the natural environment if naturally occurring) and thus, altered by the "hand of man" from its natural state.

Of the promoters isolated by the present inventors, 10 kDa rice prolamin promoter resulted in an interesting observation. In testing seed specific promoter activity, it was found that when the Nos terminator was linked downstream of 10 kDa prolamin promoter, gene expression was induced not only in seeds but also in the phloem of roots, stalks, and the like. However, when the original 3'-untranslated region (0.3 kb; SEQ ID NO: 8) was linked, gene expression other than in seeds was clearly suppressed. Thus, the inventors discovered that the 3'-untranslated region of the rice 10 kDa prolamin promoter can suppress gene expression in tissues other than seed endosperm, and is therefore required for endosperm-specific gene expression. The inventors had previously found that a foreign gene product could be expressed in seeds at a high level by inserting the 5'-untranslated region between a promoter ensuring expression in seeds and a foreign gene (JP-A 2002-58492). This seed storage protein gene is the first case for which both the 3'-flanking region and the 5'-flanking region have been identified as necessary for seed specific expression.

Endosperm-specific gene expression, where gene expression in tissues other than endosperm is suppressed, is made possible by inserting the 3'-untranslated region downstream of a promoter that comprises activity in tissues in addition to endosperm.

Thus, the present invention further provides (1) DNAs comprising a 3'-untranslated region of SEQ ID NO: 8, (2) vectors comprising the 3'-untranslated region, (3) vectors comprising a promoter and the 3'-untranslated region, (4) vectors comprising a promoter, a gene, and the 3'-untranslated region, (5) cells and transformed plants carrying the vector of (4), (6) reproductive materials of the transformed plants, and (7) methods of inducing endosperm-specific gene expression by using the 3'-untranslated region.

Seeds are essentially storage organs, and contain a large space for accumulating foreign gene products. Enzymes, antibodies, and the like that are accumulated in seeds are stable for more than one year, even when stored at room temperature. In addition, there is no need to purify such proteins if they are taken as food. Thus, useful products can be produced for extremely low costs. Furthermore, no special production facilities are required, other than agricultural fields, and they are safe from the risk of contamination by animal viruses and such.

The promoters of the present invention are especially valuable as promoters for the production of useful products using seeds. For example, these promoters enable the large-scale production of medicinal products (e.g., vaccines, antibodies, blood products, and interferons) or industrial enzymes in seeds. In addition, they can be used to express allergen epitopes in plants, creating plant crops for the treatment of allergies such that eating the seed of such a plant can treat pollinosis, house dust allergies, and the like. These promoters also enable the expression in a seed of a foreign gene whose product is highly nutritious, thus improving the nutritional value of the seed. Furthermore, it is possible to use the above promoters to create functional seeds by expressing functional peptides or functional proteins that comprise the effect of reducing high blood pressure, serum cholesterol, blood sugar, or such in seeds.

In addition, the set of promoters of this invention, which enable the expression of a gene in a desired region of a seed and a desired stage of seed development, can be used as important tools for metabolic engineering utilizing seeds. For example, by using a promoter that directs expression to the aleurone layer or embryo, a metabolic process of interest in fatty acid metabolism can be controlled.

Any patents, patent applications, and publications cited herein are incorporated by reference.

EXAMPLES

This invention will be explained in detail below with reference to Examples, but it is not to be construed as being limited thereto.

Example 1

Construction of the Promoter-GUS Gene Chimeric Constructs and Isolation of Transgenic Plants The expression patterns and promoter activity of a number of genes expressed in seeds were characterized, instead of examining the genes presumed to be regulatory factors. Fifteen different promoters ranging in size from 0.8 to 2.4 kb were isolated by PCR using genomic DNA or genomic clones as a template.

The genes and the size of their corresponding promoters are as follows: rice 10 kDa prolamin, 0.8 kb; rice 13 kDa prolamin (PG5a), 0.9 kb; rice 16 kDa prolamin, 0.9 kb; rice glutelin GluB-4, 1.4 kb; rice embryo globulin (REG2), 1.3 kb; rice 18 kDa oleosin (Ole18), 1.3 kb; rice glutamate synthase gene (GOGAT), 0.8 kb; rice pyruvate orthophosphate dikinase (PPDK), 0.8 kb; rice ADP-glucose pyrophosphorylase (AGPase), 2.0 kb; rice starch branching enzyme (SBE1), 2.0 kb; and soybean β-conglycinin, 1.0 kb. Rice glutelin GluB-1, 1.3 kb, 2.3 kb; rice glutelin GluB-2, 2.4 kb; rice alanine aminotransferase (AlaAT), 1 kb; rice 26 kDa globulin (Glb-1), 1.0 kb; and maize ubiquitin promoter, 2 kb.

Of these, the promoter sequences of 2.3 kb GluB-1, GluB-4, 10 kDa prolamin, 16 kDa prolamin, rice embryo globulin, rice oleosin, and rice ADP-glucose pyrophosphorylase are shown by SEQ ID NOs: 1 to 7, and the sequences of the primer pairs used to isolate these promoters are shown by SEQ ID NOs: 9 to 22, respectively.

Fragments of various promoters were inserted into the modified binary vector pGPTV-35S-HPT, which comprises the hygromycin phosphotransferase (HPT) gene as a selection marker (FIG. 1). The modified vector was constructed from the pGPTV-HPT binary vector (Becker et al. (1992)) using the Nos promoter as the HPT gene promoter instead of the 0.8 kb CaMV35S promoter. The seed gene promoters to be tested were introduced upstream of the UdiA gene encoding β-glucuronidase (GUS) in the modified binary vector.

Transgenic rice plants (*Oryza sativa* cv Kitaake) were created using *Agrobacterium*-mediated transformation. The plasmids constructed as above were introduced into EHA105 strain *Agrobacterium tumefaciens* by electroporation. Five-week-old calluses derived from mature rice seeds were treated with the transformed *A. tumefaciens* for three days. Each of the infected calluses was continuously cultured for four weeks in N6 selection media comprising hygromycin, and MS regeneration media. Regenerated young plants were transferred to an incubator (Goto et al., Nature Biotech., 17, 282-286 (1999)).

More than 20 different lines of independent transgenic plants were generated for each construct. The presence of the promoter fusions of interest was confirmed by PCR using genomic DNAs isolated from the leaves of independent transgenic rice lines, and the positive lines were used to characterize the promoter.

Example 2

Activity of the Seed Storage Protein Gene Promoters in Seeds

Transgenic rice seeds were examined by histochemical staining to identify the site of GUS reporter gene expression, which was induced by the seed storage protein promoters. For histochemical analysis, maturing seeds in a stage 17 days after flowering (DAF) were sectioned along their longitudinal axis with a razor blade, and the sections were incubated in 50 mM sodium phosphate buffer (pH 7.0) containing 0.5 mM X-Gluc (5-bromo-4-chloro-3-indolyl-glucuronide) and 20% methanol at 37° C. The optimal incubation time for the staining reaction varied from 30 minutes to overnight, depending on the level of GUS activity.

Figure 2:
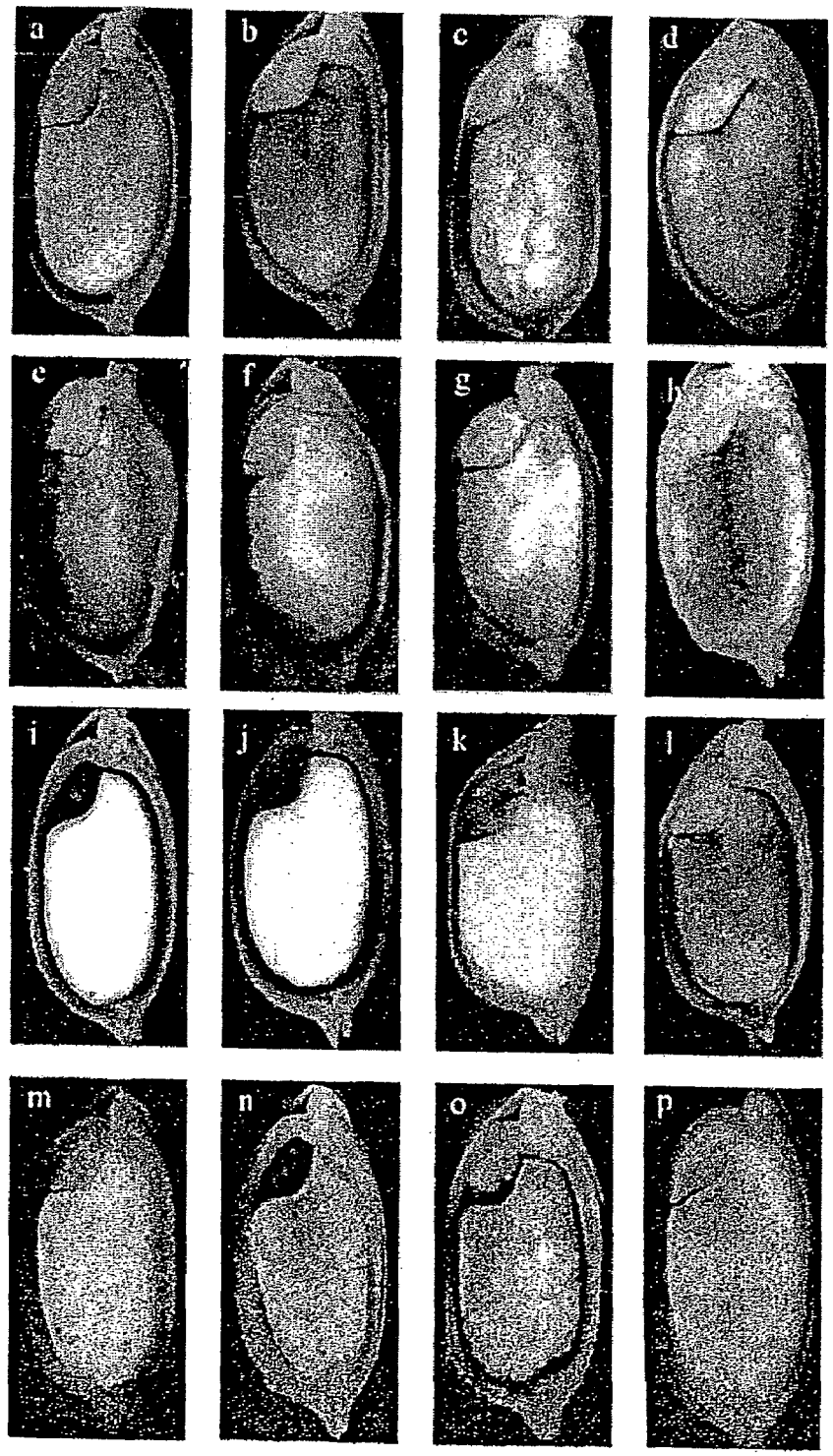
FIG. 2 is a series of pictures depicting the results of histochemical analysis of GUS expression induced by the gene promoters of various seed storage proteins and non-storage proteins. The GUS protein was detected by vertically dissecting transgenic seeds by hand, and incubating the sections in a solution containing X-Gluc. a, 1.3 kb GluB-1 promoter; b, 2.3 kb GluB-1 promoter; c, GluB-2 promoter; d, GluB-4 promoter; e, 10 kDa prolamin promoter; f, 13 kDa prolamin (PG5a) promoter; g, 16 kDa prolamin promoter; h, 26 kDa Glb-1 promoter; i, REG2 promoter; j, Ole18 promoter; k, β-conglycinin promoter; l, AlaAT promoter; m, GOGAT promoter; n, AGPase promoter; o, PPDK promoter; and p, SBE1 promoter.

FIG. 2 shows the detected expression patterns. Rice glutelin promoters (1.3 kb and 2.3 kb GluB-1, GluB-2, and GluB-4; FIG. 2a to d) and prolamin promoters (10 kDa, 13 kDa, and 16 kDa; FIG. 2e to g) induced GUS gene expression in endosperm. GUS gene expression by the glutelin promoters and prolamin promoters was also detected in aleurone layer and subaleurone tissues, but not in embryos. Further detailed examination of the maturing seeds of transgenic rice carrying the glutelin promoters and prolamin promoters revealed that the peripheral endosperm regions showed the highest GUS activity, while the inner regions showed weak activity. The GluB-1 promoters (both 1.3 kb and 2.3 kb) showed significantly higher activity in endosperm regions close to the embryo. GUS expression induced by 13 kDa prolamin promoter (PG5a) was strictly restricted to the peripheral endosperm regions. The 26 kDa globulin Glb-1 promoter induced GUS expression in the inner starchy endosperm tissue (FIG. 2h). GUS expression induced by the embryo storage protein promoters (REG2, Ole18, and β-conglycinin; FIG. 2i to k) was restricted to the embryo and aleurone tissues, and was not observed in endosperm at all. The patterns of GUS gene expression induced by these embryo storage protein promoters were almost identical. Interestingly, despite a number of reports on differential expression between monocotyledonous and dicotyledonous plants (Chowdhury et al., Plant Cell Rep., 16, 277-281 (1997); Rathaous et al., Plant Mol. Biol., 23, 613-618 (1993)), the β-conglycinin promoter from soybean, which is a dicotyledonous plant, maintained embryo-specific expression in rice, a monocotyledon. Notably, GUS expression induced by the β-conglycinin promoter was extremely low in rice, in sharp contrast to the high expression by the same promoter in the embryos and cotyledons of the dicotyledonous plant, tobacco.

Figure 3:
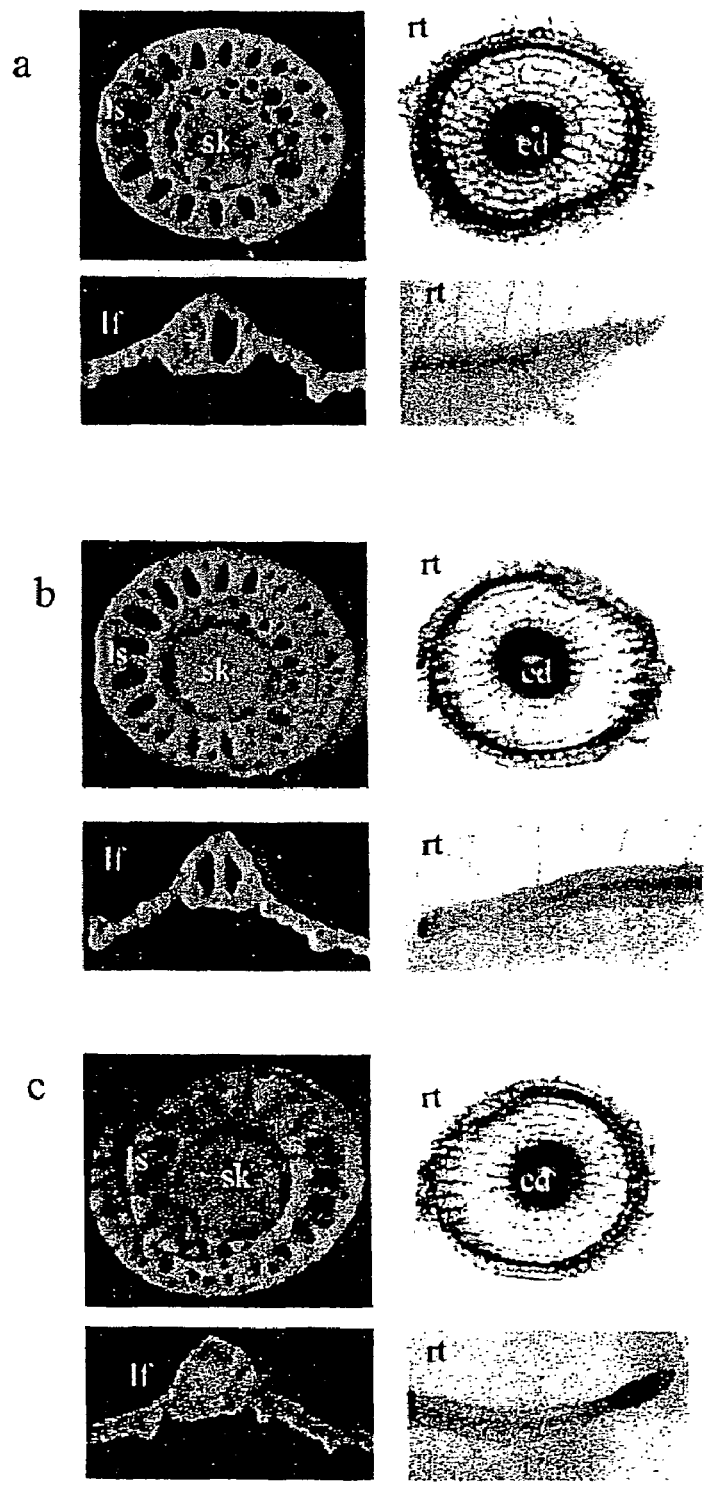
FIG. 3 is a series of pictures showing the results of histochemical analysis of GUS expression in vegetative tissues. lf, leaf; ls, leaf sheath; sk, stalk; rt, root; and ed, eudodersis. a, 10 kDa prolamin promoter; b, PPDK promoter; and c, AGPase promoter.

Overall, GUS activity was not detected in any leaves, leaf sheaths, stalks, or roots of transgenic rice comprising a fusion with a seed storage protein promoter (data not shown). The only exception was the 10 kDa prolamin promoter, which induced some expression in vegetative organs (FIG. 3). These results support the conclusion that endosperm storage protein genes (except the 10 kDa prolamin) are expressed in an endosperm-specific manner, and the expression of embryo storage protein genes are restricted to the embryo and aleurone layer.

Although the seed storage protein promoters resulted in specific gene expression in the endosperm or embryo, the promoters of non-storage proteins exhibited different expression patterns (FIG. 2). The GUS gene controlled by the AlaAT promoter was expressed in the center of starchy endosperm, and its activity was higher in the endosperm region close to the embryo (FIG. 2l). The expression pattern of the PPDK-GUS transgene was similar to that of the endosperm storage proteins (FIG. 2o). The GUS gene controlled by the AGPase promoter was expressed over the entire seed, including the pericarp, and was highly expressed in the inner starchy endosperm and embryo in particular (FIG. 2n). In contrast, the GOGAT and SBE promoters induced GUS gene expression mainly in the scutellum (the of embryo and endosperm boundary) (FIGS. 2-m and 2-p).

Example 3

GUS Expression Pattern in the Vegetative Organs

Most of the examined promoters showed either endosperm- or embryo-specific GUS gene expression. However, GUS activity was also detected in the vegetative tissues of transgenic rice comprising the promoters of the 10 kDa prolamin, PPDK, and AGPase genes (FIG. 3), and those comprising the AlaAT promoter (Kikuchi et al., Plant Mol. Biol., 39, 149-159 (1999)). In these transgenic rice plants, GUS activity was detected in leaves, leaf sheaths, and the phloem of vascular bundles in stalks, in addition to in the endosperm or over the entire seed (FIG. 3a to c). GUS activity was also detected in the endodermis of the roots of the transgenic rice. However, the expression pattern obtained with the AGPase promoter was slightly different from those obtained with the PPDK and 10 kDa prolamin promoters. In particular, the AGPase promoter induced high level GUS expression in the apical meristem, whereas the latter two induced ubiquitous staining in the root. Furthermore, the AGPase promoter showed distinct GUS activity in the root, and it was stronger than PPDK and 10 kDa prolamin promoters.

In its natural state, the 10 kDa prolamin gene is normally expressed in endosperm undergoing maturation, and not detectable in vegetative tissues. The ectopic expression of the GUS fusion product observed herein was reversed to a normal endosperm-specific expression pattern by substituting the Nos terminator with the 0.3 kb region located downstream of the stop codon of the 10 kDa prolamin gene in its natural state (data not shown). Notably, this substitution of the 3'-transcription termination region had almost no influence on the activity of the promoter. These results indicate that the endosperm specific expression of 10 kDa prolamin gene requires both 5'- and 3'-flanking regions.

SEQ ID NOs: 23 and 24 show the primer pair used to isolate the 3'-transcription termination region.

Example 4

Promoter Activity During Seed Development

The expression pattern of introduced genes in developing seeds was examined by the histochemical staining of vertical sections of seeds collected at 7, 12, and 17 DAF. Specifically, seeds undergoing maturation in stages 7, 12, and 17 days after flowering (DAF) were sectioned along their longitudinal axis with a razor blade, and the cut sections were incubated in 50 mM sodium phosphate buffer (pH 7.0) containing 0.5 mM X-Gluc (5-bromo-4-chloro-3-indolyl-glucuronide) and 20% methanol at 37° C. The optimal incubation time for the staining reaction varied from 30 minutes to overnight, depending on the level of GUS activity.

Figure 4:
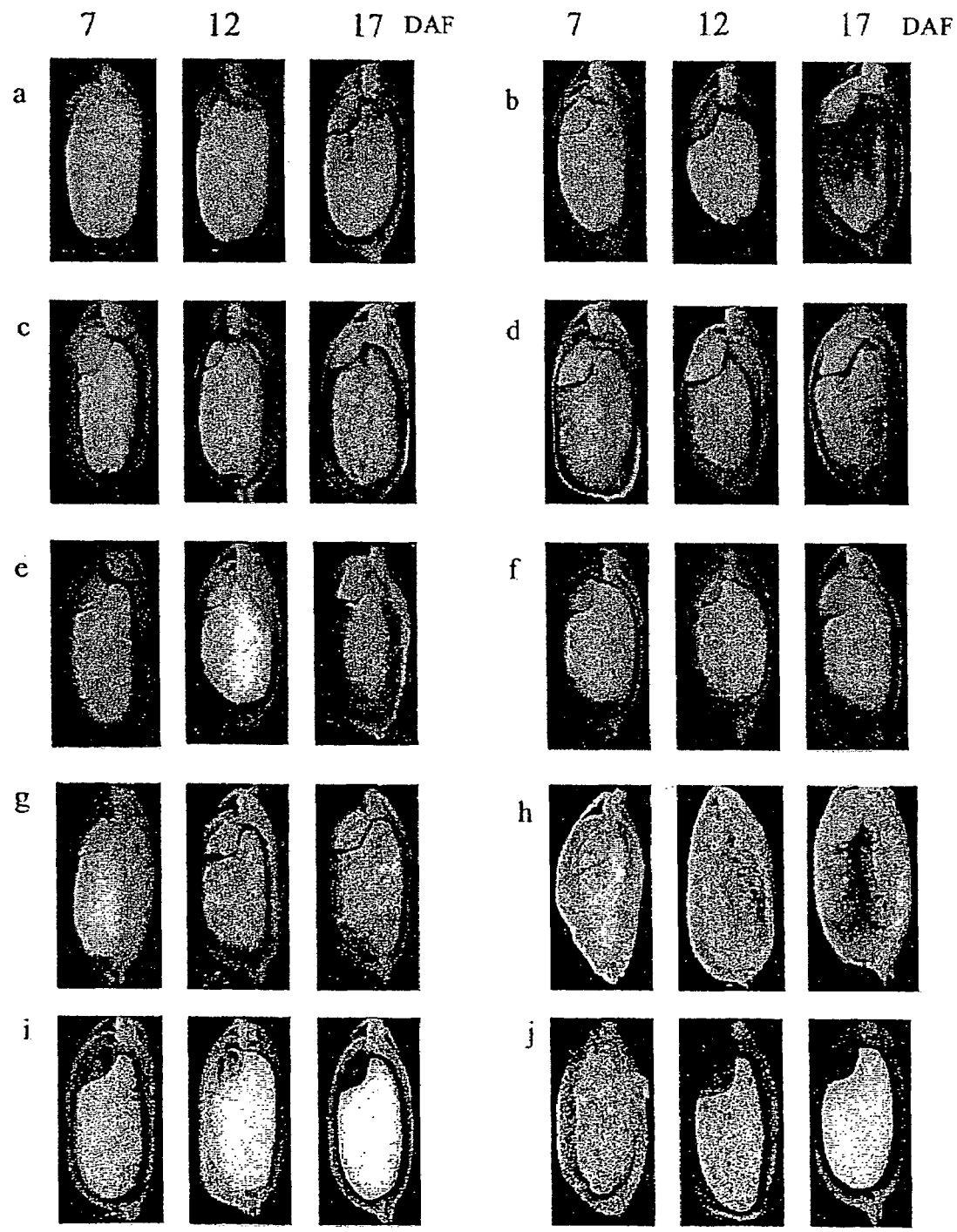
FIG. 4 is a series of pictures showing the time course of changes in GUS activity induced by seed promoters, over the maturation stages of seed development. It shows the results of histochemical staining, using X-Gluc, of the vertical sections of transgenic rice seed at 7, 12, and 17 DAF. a, 1.3 kb GluB-1 promoter; b, 2.3 kb GluB-1 promoter; c, GluB-2 promoter; d, GluB-4 promoter; e, 10 kDa prolamin promoter; f, 13 kDa prolamin (PG5a) promoter; g, 16 kDa prolamin promoter; h, 26 kDa Glb-1 promoter; i, REG2 promoter; and j, Ole18 promoter.
Figure 5:
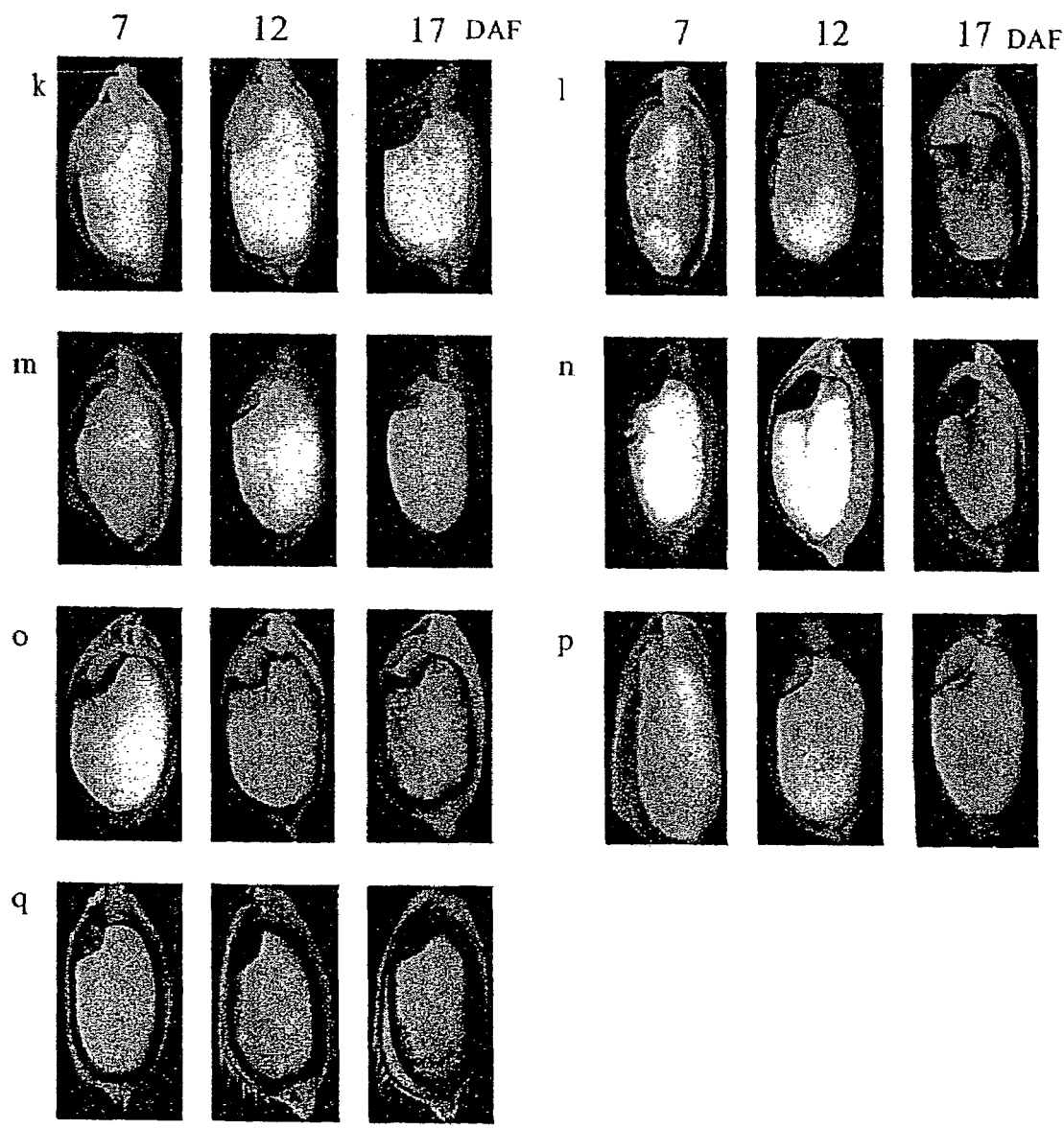
FIG. 5 continues from FIG. 4 and is a series of pictures. k, β-conglycinin promoter; l, AlaAT promoter; m, GOGAT promoter; n, AGPase promoter; o, PPDK promoter; p, SBE1 promoter; and q, ubiquitin promoter.

The expression pattern during seed maturation was examined for each transgenic line, and FIGS. 4 and 5 show the results of each representative line for each seed promoter. Interestingly, the site where GUS expression was first detected differed for each construct. The glutelin promoter and prolamin promoter first showed blue GUS staining in the peripheral endosperm regions, i.e., the aleurone and subaleurone tissues. In the glutelin promoter and 16 kDa prolamin promoter, staining then spread to the inner starchy endosperm as the seed matured (17 DAF), while this was not observed for the 10 kDa and 13 kDa prolamin promoters (FIG. 4a to g). This expression pattern was in marked contrast to the pattern with the 26 kDa Glb-1 promoter, where blue GUS staining was first detected in the inner starchy endosperm cells close to the embryo, and did not change during the development process (FIG. 4h).

GUS gene expression induced by the REG2, Ole18, and β-conglycinin gene promoters was detected by seven days after flowering (DAF). Their activity tended to be observed first in the aleurone layer, and later in the embryo. Expression by these promoters was restricted to the aleurone tissue and embryo (FIG. 4i, j, and FIG. 5k).

FIGS. 5l to p show the temporal expression patterns of non-storage protein promoters during seed maturation in representative transgenic lines. GUS expression by the AlaAT promoter was first observed in the inner starchy endosperm tissue, and eventually spread through the entire endosperm, although the embryo remained unstained (FIG. 5l). GUS activity by the SBE1 promoter was also restricted to the inner starchy endosperm tissue, and in particular, the tissue close to the embryo (FIG. 5p). However, because of the extremely low level of GUS activity, the blue staining was not detectable until 12 DAF. In contrast, when the AGPase gene promoter fusion was introduced, GUS staining first appeared in the embryo, and later spread into the center of the endosperm. Blue GUS staining was finally observed all throughout seeds undergoing maturation, with the most intense staining found in the embryo (FIG. 5n). This expression profile during seed development was very similar to that observed for the ubiquitin promoter (FIG. 5q). In contrast, the expression pattern with the PPDK promoter was similar to those with the glutelin promoter and prolamin promoter (FIG. 5o). GUS activity by the GOGAT promoter was restricted to the scutellum, and there was no particular change during seed development, except that GUS activity was not detectable at 7 DAF (FIG. 5m).

Example 5

Quantitative Analysis of the Promoter Activity

To evaluate the activity of various promoters, GUS fluorescence was assayed by the method of Jefferson (1987). Maturing seeds at 17 DAF were homogenized in GUS extraction buffer (50 mM NaPO$_4$ [pH 7.0], 10 mM 2-mercaptoethanol, 10 mM Na$_2$-EDTA, 0.1% SDS, 0.1% Triton X-100). After centrifugation, 10 μl of the supernatant was mixed with 90 μl of assay buffer containing 1 mM 4-methylumbelliferyl-β-D-glucuronide (MUG). After incubating for one hour at 37° C., 900 μl of 0.2 M Na$_2$CO$_3$ was added to the mixture to terminate the reaction. Values obtained using a fluorometer were compared with those obtained from serial dilutions of 4-methylumbelliferone (4MU). The protein amount was determined using a BIG-RAD Protein Assay kit, with serum albumin as the standard. Three seeds were assayed for each transgenic plant.

Figure 6:
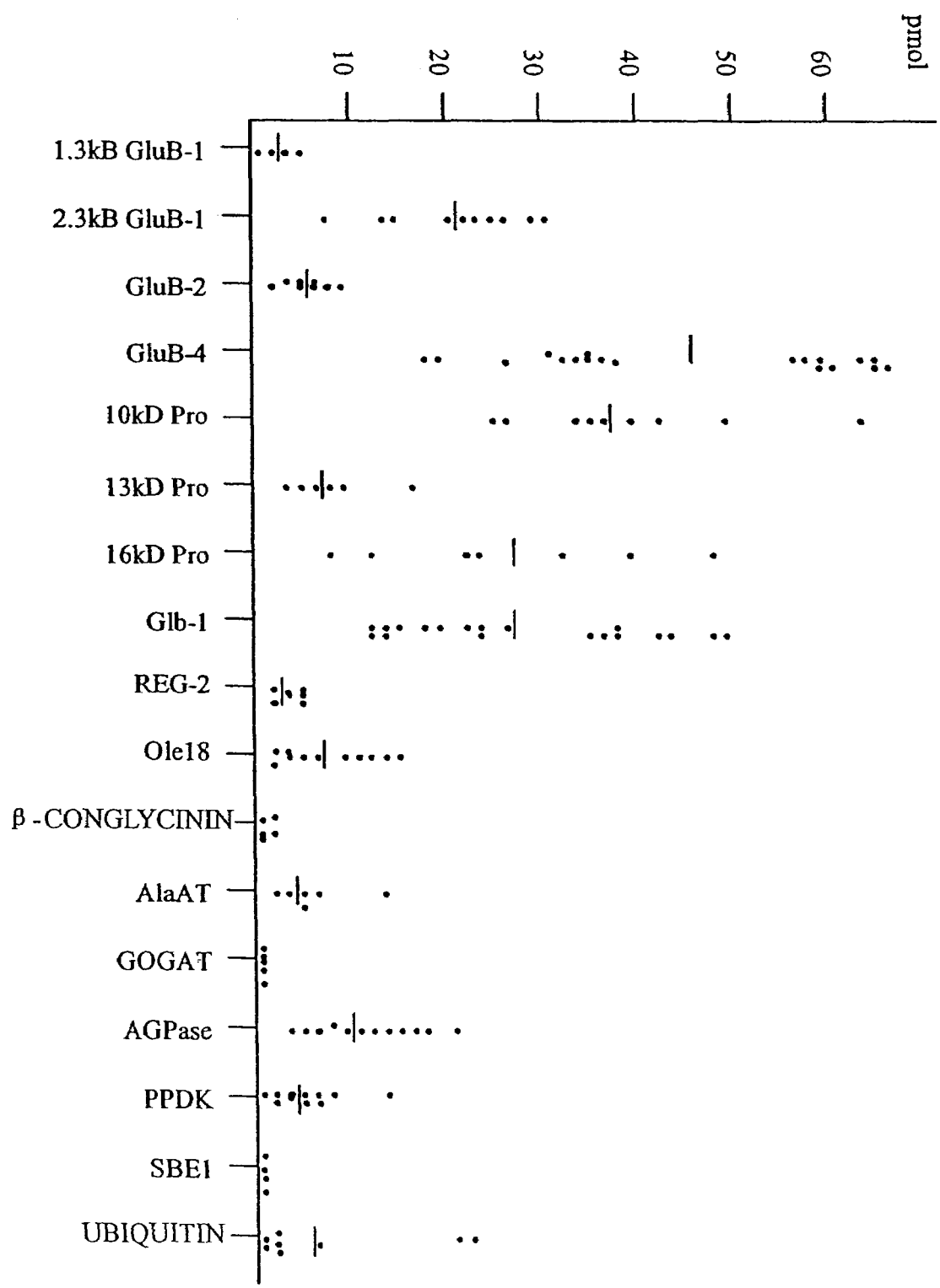
FIG. 6 shows the results of measuring the GUS activity expressed by the various promoters in maturating seed at 17 DAF. GUS activity is expressed in pmol 4 MU/min/µg protein units.

As shown in FIG. 6, significant differences were found between the promoter activities. The tested seed promoters were classified into four groups based on their activity. The group showing high GUS activity comprises the following four promoters: GluB-4, 10 kDa prolamin, 16 kDa prolamin, and Glb-1 promoters. The average GUS activities of these promoters were 44.8±16.5, 38.8±10.8, 27.1±12.7, and 28.6±11.8 pmol 4 MU/min/μg protein, respectively. The group with moderate GUS activity includes the following 2.3 kb GluB-1 and AGPase gene promoters. Their GUS activity is lower than that observed for the high activity group, but is much higher than for the other groups. The average GUS activities of 2.3 kb GluB-1 and AGPase gene promoters were 21.3±7.0 and 10±4.7 pmol 4 MU/min/μg protein, respectively. Seven promoters, i.e., 1.3 kb GluB-1, GluB-2, 13 kDa prolamin, REG-2, Ole18, AlaAT, and PPDK promoters, were tentatively grouped into a group with relatively low GUS activity. The average GUS activities of these promoters were 2.1±1.2, 5.5±2.2, 7.4±5.5, 2.4±1.2, 2±4.6, 5.9±4.0, and 4.0±3.0 pmol 4 MU/min/μg protein, respectively. The remaining three promoters, the GOGAT, SBE1, and β-conglycinin gene promoters, were grouped into the low GUS activity group. The GUS expression induced by these promoters was very faint, with activity below 1 pmol 4 MU/min/μg protein. The GUS activity of the control ubiquitin promoter was an average of 7.4±8.5 pmol 4 MU/min/μg protein (in maturing seeds). Although the ubiquitin promoter has been used in many applications as a general promoter, its level was about the same as those obtained with the promoters of the group with relatively low GUS activity.

For purposes of comparison, the activities of the PPDK promoter and AGPase promoter in vegetative tissues were also examined. The average GUS activities for PPDK promoter in leaf, stalk, and leaf sheath were 8.7±6.8, 3.7±3.6, and 16.3±13.9 pmol 4 MU/min/μg protein respectively, and 12.5±5.0, 40.2±28.5, and 23.2±16.6 pmol 4 MU/min/μg protein for AGPase promoter, respectively. The level of these promoter activities was about the same or even higher than those obtained with maturing seeds. In contrast, while 10 kDa prolamin promoter showed expression in vegetative tissues, its GUS activity (3.1±1.1, 6.0±2.9, and 2.3±1.0 pmol 4 MU/min/μg protein in leaf, stalk, and leaf sheath, respectively) was significantly lower than that observed with maturing seeds. While the PPDK, AGPase, and 10 kDa prolamin genes were expressed constitutively, their expression levels in various tissues varied depending on the gene.

What is claimed is:

1. An isolated DNA comprising promoter activity in plant seeds, and in the phloem of roots, leaves, and stalks; wherein the DNA consists of the nucleotide sequence of SEQ ID NO: 3.

2. An isolated DNA comprising a DNA with promoter activity in plant seeds, and in the phloem of roots, leaves, and stalks operably linked to a foreign nucleic acid of interest, wherein the DNA with promoter activity consists of the nucleotide sequence of SEQ ID NO: 3.

3. A plasmid vector comprising a DNA with promoter activity in plant seeds, and in the phloem of roots, leaves, and stalks; wherein the DNA with promoter activity consists of the nucleotide sequence of SEQ ID NO:3, and is operably linked to a foreign nucleic acid of interest.

4. A plasmid vector comprising the DNA of claim 2.

5. A plant cell transformed with the DNA of claim 2.

6. A plant cell transformed with the plasmid vector of claim 3.

7. A plant cell transformed with the plasmid vector of claim 4.

8. A transformed plant comprising the cell of claim 6.

9. A transformed plant comprising the cell of claim 7.

10. A reproductive material of the plant of claim 8, wherein said reproductive material comprises said nucleotide sequence of SEQ ID NO: 3 and said foreign nucleic acid of interest.

11. A reproductive material of the plant of claim 9, wherein said reproductive material comprises said nucleotide sequence of SEQ ID NO: 3 and said foreign nucleic acid of interest operably linked to the promoter.

12. The reproductive material of claim 10, wherein the reproductive material is a seed.

13. The reproductive material of claim 11, wherein the reproductive material is a seed.

14. A method of expressing a nucleic acid of interest in a seed generated from a plant cell, comprising the steps of:
   (a) introducing the DNA of claim 2 into the plant cell,
   (b) regenerating a plant from the plant cell, and
   (c) growing the transgenic plant to maturity to produce seeds.

15. A method of expressing a nucleic acid of interest in a seed generated from a plant cell, comprising the steps of:
   (a) introducing the vector of claim 3 into the plant cell,
   (b) regenerating a plant from the plant cell, and
   (c) growing the transgenic plant to maturity to produce seeds.

16. A method of expressing a nucleic acid of interest in a seed generated from a plant cell, comprising the steps of:

(a) introducing the vector of claim 4 into the plant cell,
(b) regenerating a plant from the plant cell, and
(c) growing the transgenic plant to maturity to produce seeds.

17. An isolated DNA, wherein the DNA consists of the nucleotide sequence of SEQ ID NO: 8.

18. A plasmid vector comprising a DNA consisting of the nucleotide sequence of SEQ ID NO: 8 operably linked to a foreign nucleic acid of interest.

19. A plasmid vector comprising the promoter of SEQ ID NO:3 operably linked to a foreign nucleic acid of interest which is further operably linked to the 3'-untranslated region of SEQ ID NO: 8; wherein the foreign nucleic acid is expressed in a seed specific manner when said vector is introduced into a plant.

20. An isolated DNA comprising the promoter of SEQ ID NO:3 overably linked to a foreign nucleic acid of interest which is further operably linked to the 3'-untranslated region as shown in SEQ ID NO: 8; wherein the foreign nucleic acid is expressed in a seed specific manner when said DNA is introduced into a plant.

21. A plasmid vector comprising the DNA of claim 20.

22. A method of expressing a nucleic acid of interest in a seed generated from a plant cell, comprising the steps of:
(a) introducing the DNA of claim 20 into the plant cell,
(b) regenerating a plant from the plant cell, and
(c) growing the transgenic plant to maturity to produce seeds.

23. A method of expressing a nucleic acid of interest in a seed generated from a plant cell, comprising the steps of:
(a) introducing the plasmid vector of claim 21 into the plant cell,
(b) regenerating a plant from the plant cell, and
(c) growing the transgenic plant to maturity to produce seeds.

* * * * *

UNITED STATES PATENT AND TRADEMARK OFFICE
CERTIFICATE OF CORRECTION

PATENT NO.         : 7,595,384 B2
APPLICATION NO.    : 11/644759
DATED              : September 29, 2009
INVENTOR(S)        : Takaiwa et al.

It is certified that error appears in the above-identified patent and that said Letters Patent is hereby corrected as shown below:

On the Title Page, item [56]: Column 2, "Other Publications," Line 25, "Rice Gluetelin Gene" should be changed to --Rice Glutelin Gene--

Second Page, Column 2, "Other Publications," Line 24, "Blub-1 Gene for" should be changed to --GluB-1 Gene for--

Second Page, Column 2, "Other Publications," Line 38, "Phrophosphorylase Subunit" should be changed to --Pyrophosphorylase Subunit--

Column 6, Line 9, "(Proc. Nati. Acad. Sci. U.S.A.," should be changed to

--Proc. Natl. Acad. Sci. U.S.A.,--

Column 14, Line 1, "a BIG-RAD Protein Assay" should be changed to --a BIO-RAD Protein Assay--

Column 29, Line 56, "SEQ ID NO:3," should be changed to --SEQ ID NO: 3,--

Column 31, Line 11, "NO:3 overably linked" should be changed to --NO: 3 operably linked--

Signed and Sealed this

Ninth Day of March, 2010

David J. Kappos
*Director of the United States Patent and Trademark Office*

SEQUENCE LISTING

```
<160> NUMBER OF SEQ ID NOS: 24

<210> SEQ ID NO 1
<211> LENGTH: 2349
<212> TYPE: DNA
<213> ORGANISM: Oryza sativa

<400> SEQUENCE: 1
tctagacaga ttcttgctac caacaacttc acaaagtagt agtcaaccaa aactatgcta      60
aggaatcacc tcacttccgc ccatgaccgt gagcacgact gttcaaacag tttgttaatc     120
```

```
tctacaaaga aggtacactt tacctacaca acgccactaa cctgagttac ccagcccatg    180
caaaatagcc acgtcttgtg acttaaggga tttcgcgaca aggcatttcg aaagcccaca    240
caaggacacc ttatgaaaac tggaggggtc ccacagacca acaacaagtt aggtcccaaa    300
ccatgttgtg ccaggaaaaa tccaagggt cctccccaac accaccccga caaatccact     360
tgtccattgg catcaagatt tgcctgacct agctaattac tcagccaggc atgtcacaat    420
tcacccatgt ggtcacacat gttaggttgg agaaattcta aaggaaagga atcggtccat    480
atgagcaaga ccgagaaacc ataccaccag tacttctacc gaaatacgag tttagtaaac    540
tcatttgttt tcaaggcacc cgacccaggt gtgtcgggtt ttccagggat tttgtaaacc    600
caagttttac ccatagttga tcattcaaat tttgaggagg gtcattggta tccgtacctg    660
agggcacgaa tactgagacc tagcattgta gtcgaccaag gaggttaatg cagcaattgt    720
aggtggggcc tgttggttat attgcaaact gcggccaaca tttcatgtgt aatttagaga    780
tgtgcatttt gagaaatgaa atacttagtt tcaaattatg ggctcaaata atgaaaggtg    840
acctaccttg cttgatatct tgagcttctt cctcgtattc cgcgcactag agatcttct    900
ggctccgaag ctacacgtgg aacgagataa ctcaacaaaa cgaccaagga aaagctcgta    960
ttagtgagta ctaagtgtgc cactgaatag atctcgattt ttgaggaatt ttagaagttg   1020
aacagagtca atcgaacaga cagttgaaga gatatggatt ttctaagatt aattgattct   1080
ctgtataaag aaaaaaagta ttattgaatt aaatggaaaa agaaaaagga aaagggat    1140
ggcttctgct ttttgggctg aaggcggcgt gtggccagcg tgctgcgtgc ggacagcgag   1200
cgaacacacg acggagcagc tacgacgaac ggggaccga gtggaccgga cgaggatgtg    1260
gcctaggacg agtgcacaag gctagtggac tcggtcccg cgcggtatcc cgagtggtcc    1320
actgtctgca aacacgattc acatagagcg ggcagacgcg ggagccgtcc taggtgcacc   1380
ggaagcaaat ccgtcgcctg ggtggatttg agtgacacgg cccacgtgta gcctcacagc   1440
tctccgtggt cagatgtgta aaattatcat aatatgtgtt tttcaaatag ttaaataata   1500
tataggca agttatatgg gtcaataagc agtaaaaagg cttatgacat ggtaaaatta    1560
cttacaccaa tatgccttac tgtctgatat attttacatg acaacaaagt tacaagtacg   1620
tcatttaaaa atacaagtta cttatcaatt gtagtgtatc aagtaaatga caacaaacct   1680
acaaatttgc tattttgaag gaacacttaa aaaaatcaat aggcaagtta tatagtcaat   1740
aaactgcaag aaggcttatg acatggaaaa attacataca ccaatatgct ttattgtccg   1800
gtatatttta caagacaaca aagttataag tatgtcattt aaaaatacaa gttacttatc   1860
aattgtcaag taaatgaaaa caaacctaca aatttgttat tttgaaggaa cacctaaatt   1920
atcaaatata gcttgctacg caaaatgaca acatgcttac aagttattat catcttaaag   1980
ttagactcat cttctcaagc ataagagctt tatggtgcaa aaacaaatat aatgacaagg   2040
caaagataca tacatattaa gagtatggac agacatttct ttaacaaact ccatttgtat   2100
tactccaaaa gcaccagaag tttgtcatgg ctgagtcatg aaatgtatag ttcaatcttg   2160
caaagttgcc tttcctttg tactgtgttt taacactaca agccatatat tgtctgtacg    2220
tgcaacaaac tatatcacca tgtatcccaa gatgcttttt tattgctata taaactagct   2280
tggtctgtct ttgaactcac atcaattagc ttaagtttcc ataagcaagt acaaatagcc   2340
atgggatcc                                                           2349
```

<210> SEQ ID NO 2
<211> LENGTH: 1489

```
<212> TYPE: DNA
<213> ORGANISM: Oryza sativa

<400> SEQUENCE: 2
tacagggttc cttgcgtgaa gaagggtggc ctgcggttca ccattaacgg tcacgactac      60
ttccagctag tactggtgac aacgtcgcg gcggcagggt caatcaagtc catggaggtt     120
atgggttcca acacagcgga ttggatgccg atggcacgta actggggcgc ccaatggcac    180
tcactggcct acctcaccgg tcaaggtcta tcctttaggg tcaccaacac agatgaccaa    240
acgctcgtct tcaccaacgt cgtgccacca ggatggaagt tggccagac atttgcaagc    300 aagctgcagt tcaagtgaga ggagaagcct gaattgatac cggagcgttt cttttgggag    360
taacatctct ggttgcctag caaacatatg attgtatata agtttcgttg tgcgtttatt    420
ctttcggtgt gtaaaataac atacatgctt tcctgatatt ttcttgtata tatgtacaca    480
cacacgacaa atccttccat ttctattatt attgaacaat taattgcga gggcgagtac     540 ttgtctgttt acctttttt tttcagatgg catttatag tttaaccttt catggaccgg       600
cagtagttct aaccatgaat gaaagaaat catagtccac accacgcagg acattgtgg      660 tcatttagga caagacgatt tgattaatgt cttgtatgat atggtcgaca gtgaggacta    720
acaaacatat ggcatatttt attaccggcg agttaaataa atttatgtca cagtaataaa    780
ctgcctaata aatgcacgcc agaaaatata atgataaaaa aagaaaaga tacataagtc     840 cattgcttct actttttaa aaattaaatc caacattttc tattttttgg tataaacttg     900
gaagtactag ttggatatgc aaaatcatct aacctccata tatttcatca atttgtttac    960
tttacatatg ggagaggata gtatgtcaaa gaaatgaca acaagcttac aagtttctta    1020
ttttaaaagt tccgctaact tatcaagcat agtgtgccac gcaaaactga caacaaacca   1080
acaaatttaa ggagcgccta acttatcatc tatgacatac cgcacaaaat gataacatac   1140
tagagaaact ttattgcaca aaaggaaatt tatcccataag gcaaaggaac atcttaaggc   1200
tttggatata catttaccaa caagcattgt ttgtattacc cctaaagcgc aagacatgtc    1260
atccatgagt catagtgtgt atatctcaac attgcaaagc taccttttt ctattatact    1320 tttcgcatta taggctagat attatctata catgtcaaca aactctatcc ctacgtcata   1380
tctgaagatt ctttctttca ctatataagt tggcttccct gtcattgaac tcacatcaac   1440
cagcccaagt ttccaataac atcctcaaat agctatggcg accatagct              1489

<210> SEQ ID NO 3
<211> LENGTH: 834
<212> TYPE: DNA
<213> ORGANISM: Oryza sativa

<400> SEQUENCE: 3
actggataat tataatatca gttaaaattg aaaataatgc aacttcatac ttgcatggtg      60
tcagtagtgc ctgcctaaga aatgtgtctt gtcataatat gattacatga atatgtttta    120
cttcctcgtt tctctttatt tgtaagataa agaactagat atgtggaaag taggatagca    180
aagagtatgg ccaaactcta atctttgctt tattttttgg gatggaccca aaatttgttt    240 ctccttact tctttccctt tacaacaatg ttctttactt ccaattctta ttaacaaaac    300
tccaaataca tgccaaactg catatgtatg tatgctatta aggcacattt acaaagctcc    360
aagtttacct actcaatcat tcacatatgg cgatgactca aactcttaat tgttatctgg    420
taagctgtga cttgtgtaac acattctaca agtcccatac gaattctgtt cacaaaagtt    480
```

| | |
|---|---|
| tctttgtcca gctcataatt tacaaaactg caaaatgcca aagcaatctg gcacaacctt | 540 |
| atcatcatat tttctttcca cgcattaaag cactggcaga attatctttg tgtagatatt | 600 |
| ccaaaagtat tggttgaata aatgtccaaa taaattccat gcctcatgat ttccagctta | 660 |
| tgtggcctcc actaggtggt tttgcaaagg ccaaactctt tcctggctta cacagctacc | 720 |
| agcatgtata aataggcccc taggcaacca ttattccatc atcctcaaca atattgtcta | 780 |
| caccatctgg aatcttgttt aacactagta ttgtagaatc agcaatggca gcat | 834 |

<210> SEQ ID NO 4
<211> LENGTH: 940
<212> TYPE: DNA
<213> ORGANISM: Oryza sativa

<400> SEQUENCE: 4

| | |
|---|---|
| gatcttttaa ccgtgctacg ctgggttaat tagcgatggt gcaggtcacg tacccaaatt | 60 |
| tcttcactgt tggatcaact agagtagtta acgagggca tgtgatgaag gctagctatt | 120 |
| tgaaattttc caattatccc tgcataagtc aggctacaat agcacctgga ctacatgcag | 180 |
| ggattacaaa ataggtggta accacattta ccgcgttaac cctatcaaat tcaaataaat | 240 |
| tttaaaagta atttgatttt tttaataaat tttgtatggt ttctcaagct ttattttggt | 300 |
| taccgtgctt actgcggagg caatgggaaa ccctcactag aagttgcacc tgttcttgtc | 360 |
| tgtgcaccat atcatgttga atcatgtgcg ttgtgtcttt cggaagaacc gatttactac | 420 |
| atgactcatc aattccactt tacgtatcaa aaggtttgtt atgggggcaa tgcttttgtg | 480 |
| aaattaaatt tttattttgc gtcacgttgt atctagttaa acactaccta cctaccatta | 540 |
| caaaacctca ttccacaaaa cgatgcatct agataaaaaa tatgcacatgt aaagtgagta | 600 |
| atgactcatg tttattatca aaaatcgata acaatcaaat gatataggta gtaaagtacc | 660 |
| tttgaaatgg catgtccaag tatgtgtagc tccacctagc acaatatccc aagtgatcat | 720 |
| cataaaaggc atacaaatac aagcagccga tgatgcacac aagaaacaac acaaattgca | 780 |
| caaaaccaaa agcaaccgat gccttgagca tagagatcat gctattccca ctataaatac | 840 |
| aaatgcacca tatcaagatg ctcctcaccc ttactgaaaa atcacaaaca tcaaaacgtt | 900 |
| ataagagttc tctagcatcc atcacatagc catgaagatc | 940 |

<210> SEQ ID NO 5
<211> LENGTH: 1335
<212> TYPE: DNA
<213> ORGANISM: Oryza sativa

<400> SEQUENCE: 5

| | |
|---|---|
| cgcggcacgg gcggttcagc gtgctggaga ggtttccccg acgagcaggt ggtgggcgcc | 60 |
| gccgtcgggg ggtacagacc gtcgacgagc gagtcattag ctagtatagc tatctagggt | 120 |
| gacgtgcaca taatacatgt gcagaagtgt tgtacagtac tactacgttc tactgttggt | 180 |
| gacccggctg ggccgccgta cgtcgtgatg actgaccttg ctgcggattc gccggcgagc | 240 |
| agccgcgcgc acgcgtgcgg cgtctggtga tgcaacagcg gcgagatatc gatccaccgg | 300 |
| agaattaacg cgcgcgcatt catgcaggtt ggtcgttgat catgtactgt aatggagtag | 360 |
| tgtacacgcc ggcacgcgca gcttgcattg cagcgtgtcg tagtgtgcag tggaaccact | 420 |
| cttgacattt ttattttttct tgtgaagagt agtactacac ctcagggcat gctagcctat | 480 |
| ggctgtgtta ggtttcacgc taaaattaga agtttaaaga aattgaaacg gtgtgatgga | 540 |
| aaagttgaaa gtttctttgt attggaaagt tcgatgtgac ggaaaagtta taagtttaaa | 600 |

```
aaaaaagttg aaatctaaac aggcctatgt tgttctctct tatgtgtaat ttgctacatt    660
gccactttca acattatcaa attctggcat tactattatt ttgataagcc aacaaactaa    720
acatatttca ttcattacta ccttaccaaa ttttgataat tctataagct tcctctctta    780
aaactctatc aaaatttaat aaacatcaaa actatcaaaa attaataatg ccaaaattta    840
gcactattaa aatggcaaca aagtgaacaa gctgtaagtt gggaaaaaaa aagtgacaac    900
cgagccagca acctgtccca aaggcccacg caatcgacta aagccaata ttgggcccga     960
gaaaatggcc caacacacgt atcggcccgc ccatgaagtg gattggaatt tgcaacaacc   1020
caggaaaaca cggcccacac cagggtgcaa ccgcatttgt tcccatccat ctcggccctg   1080
tcgccattgt gccaaacagc tagcgcgact acagcgacgc cgcacgccgc ccccagcac    1140
acgcaccgcc gcgctccaca tgcgccacgc caacacatcc gcttcggctc gccacgtacg   1200
cacccccaac ctccacctgg caccgcgcat ggccgcaatg ccaccccctc gcacagtcgc   1260
actcccctac ataagccatc actcctctca tcacctccac ccaaacgcca ccgctaggat   1320
cgatcgaaca ccatg                                                    1335

<210> SEQ ID NO 6
<211> LENGTH: 1249
<212> TYPE: DNA
<213> ORGANISM: Oryza sativa

<400> SEQUENCE: 6
gatggtcagc caatacattg atccgttgcc aatcatgcaa agtatttggg ctgtggccga     60
gtgccggaat tgataattgt gttctgacta aattaaatga ccagaagtcg ctatcttcca    120
atgtatccga aacctggatt aaacaatcct gttctgttct ctagcccctc ctgcatggcc    180
ggattgtttt tttgacatgt tttcttgact gaggcctgtt tgttctaaac ttttttcttca   240
aactttttaac tttttcatca catcagaact tttctacaca tataaacttt taactttttcc   300
gtcacatcgt tccaatttca atcaaacttt caattttggc gtgaactaaa cacaccctga    360
gtctttttatt gctcctccgt acgggttggc tggttgagaa taggtatttt cagagagaaa    420
atctagatat tgggaggaac ttggcatgaa tggccactat atttagagca attctacggt    480
ccttgaggag gtaccatgag gtaccaaaat tttagtgtaa attttagtat ctcattataa    540
ctaggtatta tgaggtacca aatttacaat agaaaaaata gtacttcatg gtactttctt    600
aagtaccgta aaattgctcc tatatttaag gggatgttta tatctatcca tatccataat    660
ttgatttga taagaaaaaa tgtgagcaca ccaagcatgt ccatgacctt gcactcttgg    720
ctcactcgtc aactgtgaag aacctcaaaa atgctcaata tagctacagg tgcctgaaaa    780
aataacttta aagttttgaa catcgatttc actaaacaac aattattatc tccctctgaa    840
agatgatagt ttagaactct agaatcattg tcggcggaga aagtaaatta ttttccccaa    900
atttccagct atgaaaaaac cctcaccaaa caccatcaaa caagagttca ccaaaccgcc    960
catgcggcca tgctgtcacg caacgcaccg cattgcctga tggccgctcg atgcatgcat   1020
gcttccccgt gcacatatcc gacagacgcg ccgtgtcagc gagctcctcg accgacctgt   1080
gtagcccatg caagcatcca ccccgccac gtacaccccc tcctcctccc tacgtgtcac    1140
cgctctctcc acctatatat gcccacctgg cccctctcct cccatctcca cttcaccga    1200
tcgcttcttc ttcttcttcg ttgcattcat cttgctagct agcttagca               1249

<210> SEQ ID NO 7
```

<211> LENGTH: 1961
<212> TYPE: DNA
<213> ORGANISM: Oryza sativa

<400> SEQUENCE: 7

```
aaggtttcat gcgtatcgtg acagatgtta cataatgaca aattccccag ctggagcacc      60
tttatccctg ctgtttgcat gaaattagct tgtcttgtag ttccctccag caaaaagaag     120
tctgaaacaa acaacatttt cgaaaaaaag gcatccatga gttagcattt ctacagttgt     180
ctatagaggg gaaggctgca cgacaaagtt tccaggcttg gaaacaacct cttatgtaaa     240
atttttcgta tgtatcagat gatttgtttg cgttacggca tctccaccta acatcacctt     300
catcatgcgc ctatggtctt tctcttgcct gttttatacg taaaattgga aacgacagaa     360
actttttgcca tctttattaa aggaaggcaa atatgcaaat ataggcatca agatcacagt     420
tagtggatta tcatctttgt aggttaacat gtcctacccc aggggagctt atactcaagt     480
actccatgca ttttcatgaa atgagaaaaa acgattttta agagaaatgt actttcttgt     540
atttatgcca aatggcaagg actgaaaggg aaaaactaag aaagggaacg ttacagtaag     600
gctctgtggg gactggggac ttcagagaaa cgtgaaccct gcttccttcc tctgcatgaa     660
cataacacca gaggtttcca gcctttcaca cagttgttga tggcttcaca caattcatct     720
ctacctcctg actcttttata aggaccccca gcatcaccac aattgcacaa gtacaggcat     780
tagatccaca agaacacttg ggcaggcaag cacctctttg atctttaagc cgttgttatg     840
ttctatttct gagcatatgg tttctagtta tattctttttt cttcattcgt ttcatatctt     900
tgaagtgttg atgcaaatgc ggtgaacaac tatcaactgt gtactctcca agtgaatgcg     960
aataatcatt tcctgtgaga attgtgggct agataaacga atgaaatgct gttttatcta    1020
tgtcatgtgt ggaaatttag ttaatttttcc ggtcttttta tgcattgaga tgggtatgct    1080
gtttttttag ttgggtccca tcatcttgag aattctttca aatttccttt tctttatcct    1140
atataaagga tagagaaggc gtatgcctag gtgcaccaac cctgaaagtt ttattctaat    1200
tgcgggaatg gtttgtaatt tttgcttgtt caggttcttt ttcgtggcct ttcttttttt    1260
tccccttatt ttgcttagtc tttcacagtc caattttttgg gaagtagtat atcttagttt    1320
ggtcctaagg caccatgttg tactgcagga aaaaaagag taattgtatt ctgtttttttc    1380
cttgattact atatccctgt tttaattaat tttgtgcctt tgttgtttga tgttggaact    1440
tcaatgccca taattagtca tttgacttgt tttgggtttt gacgctatct tgagtgccat    1500
aggaaactgg tagaatttag taataatttt atatagactg aatgttgagc ccaccacaaa    1560
tggtttcctt ctgtacaagt atttaataac tcaagcacag gaaacatcag atctctaatc    1620
taaaggttaa caatgggctc aagcaggagc agtagttcag ctctatctgt atatttagaa    1680
gggctggatc tacctgtcca ccagctttta attttaccct ggcagctgga taacttcttg    1740
tctgttaatt tcatttagtg ctgtgttatt ttcttcttgt tgttcaggat ggatgctttt    1800
gaatttctgg aatttcgtat tttgttctat ctctttatga aatgacgtta tggcacactt    1860
tttctgcata ttcttgatga aaataattac ctagtcattt ttttagttgc aggtttgtct    1920
gggactttga gtacccatgc aattcatgat gccattggat a                        1961
```

<210> SEQ ID NO 8
<211> LENGTH: 288
<212> TYPE: DNA
<213> ORGANISM: Oryza sativa

<400> SEQUENCE: 8

-continued

```
tcaaacgttg gttacatgta ctctagtaat aaggtgttgc atactatcgt gtgcaaacac    60
tagaaataag aaccattgaa taaaatatca atcattttca gacttgcaaa tattgggtat   120
ttggatttct gtcccatgtc cctcttgaaa gccatgctgt acatgttgga gttccccctt   180
ggacccaacc tactccatgc tcccatgttg atcttaaatt ccctgttccc ccagagcatg   240
taaattttct tatgctaatc agagcaagct cgatgtctca ttaacata                288
```

```
<210> SEQ ID NO 9
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 9
attctagaca gattcttgct accaac                                         26
```

```
<210> SEQ ID NO 10
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 10
aaccatgggc tgggccatag aaccgtggca taata                               35
```

```
<210> SEQ ID NO 11
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 11
actctagata cagggttcct tgcgtgaaga ag                                  32
```

```
<210> SEQ ID NO 12
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 12
atggatccag ctatttgagg atgttattgg aa                                  32
```

```
<210> SEQ ID NO 13
<211> LENGTH: 29
<212> TYPE: DNA
<213> ORGANISM: Artificial
<220> FEATURE:
<223> OTHER INFORMATION: an artificially synthesized primer sequence

<400> SEQUENCE: 13
tatgtcgact ggataattat aatatcagt                                      29
```

```
<210> SEQ ID NO 14
<211> LENGTH: 29
<212> TYPE: DNA
<213> ORGANISM: Artificial
<220> FEATURE:
<223> OTHER INFORMATION: an artificially synthesized primer sequence
```

<400> SEQUENCE: 14
aaggatcctg ctgattctac aatactagt            29

<210> SEQ ID NO 15
<211> LENGTH: 27
<212> TYPE: DNA
<213> ORGANISM: Artificial
<220> FEATURE:
<223> OTHER INFORMATION: an artificially synthesized primer sequence

<400> SEQUENCE: 15
aagtcgactt ttaaccgtgc tacgctg              27

<210> SEQ ID NO 16
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 16
atggatccgg ctatgtgatg gatgct               26

<210> SEQ ID NO 17
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 17
aagtcgacgc ggcacgggcg gttcagcg             28

<210> SEQ ID NO 18
<211> LENGTH: 27
<212> TYPE: DNA
<213> ORGANISM: Artificial
<220> FEATURE:
<223> OTHER INFORMATION: an artificially synthesized primer sequence

<400> SEQUENCE: 18
atggatccgg tgttcgatcg atcctag              27

<210> SEQ ID NO 19
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 19
gatggtcagc caatacattg atcc                 24

<210> SEQ ID NO 20
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 20
tgctaagcta gctagcaaga tgaa                 24

<210> SEQ ID NO 21
<211> LENGTH: 29

```
<212> TYPE: DNA
<213> ORGANISM: Artificial
<220> FEATURE:
<223> OTHER INFORMATION: an artificially synthesized primer sequence

<400> SEQUENCE: 21
aagtcgacaa ggtttcatgc gtatcgtga                                   29

<210> SEQ ID NO 22
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 22
atggatccga attgcatggg tactcaag                                    28

<210> SEQ ID NO 23
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 23
atggtacctc aaacgttggt tacatgtact c                                31

<210> SEQ ID NO 24
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 24
aaccagagct ctggtgatca aatagggata tgttaatg                         38
```